United States Patent
Misiakos et al.

(10) Patent No.: US 11,119,040 B2
(45) Date of Patent: Sep. 14, 2021

(54) PHOTONIC CHIPS WITH ONE SIDED OPTICAL PORTS SELF ALIGNED TO BIFURCATED FIBERS FOR THE LABEL FREE DETECTION OF BIOMOLECULAR REACTIONS THROUGH THE USE OF INTEGRATED INTERFEROMETERS AND RESONATORS

(71) Applicants: NCSR "DEMOKRITOS", Agia Paraskevi (GR); Konstantinos Misiakos, Agia Paraskevi (GR); Ioannis Raptis, Agia Paraskevi (GR)

(72) Inventors: Konstantinos Misiakos, Agia Paraskevi (GR); Ioannis Raptis, Agia Paraskevi (GR); Alexandros Salapatas, Agia Paraskevi (GR)

(*) Notice: Subject to any disclaimer, the term of this patent is extended or adjusted under 35 U.S.C. 154(b) by 284 days.

(21) Appl. No.: 16/344,119

(22) PCT Filed: Oct. 23, 2017

(86) PCT No.: PCT/GR2017/000062
§ 371 (c)(1),
(2) Date: Apr. 23, 2019

(87) PCT Pub. No.: WO2018/078404
PCT Pub. Date: May 3, 2018

(65) Prior Publication Data
US 2020/0064260 A1    Feb. 27, 2020

(30) Foreign Application Priority Data

Oct. 27, 2016 (GR) .............................. 20160100552

(51) Int. Cl.
*G01N 21/45* (2006.01)
*G01N 21/77* (2006.01)
(Continued)

(52) U.S. Cl.
CPC ......... *G01N 21/45* (2013.01); *G01N 21/7703* (2013.01); *G01N 33/54373* (2013.01);
(Continued)

(58) Field of Classification Search
CPC ............... G01N 21/45; G01N 21/7703; G01N 33/54373; G01N 2021/7779; G01N 21/7746; G02B 6/29352; G02B 6/30
See application file for complete search history.

(56) References Cited

U.S. PATENT DOCUMENTS 9,341,786 B1 * 5/2016 Ayliffe ................. G02B 6/4246
2004/0257579 A1   12/2004 Shirai
(Continued)

FOREIGN PATENT DOCUMENTS

EP    2180361    4/2010
FR    2761164    9/1998
(Continued)

OTHER PUBLICATIONS

Jason E. Dover, et al., "Recent advances in peptide probe-based biosensors for detection of infectious agents", Apr. 2009, Journal of Microbiological Methods, 78, 10-19 (Year: 2009).*

*Primary Examiner* — Jill A Warden
*Assistant Examiner* — Henry H Nguyen
(74) *Attorney, Agent, or Firm* — DP IP Group; Francos S. De Liguori

(57) ABSTRACT

A photonic chip has at least one input waveguide, at least one output waveguide, one of at least one Mach-Zehnder interferometer and at least one resonator, and a one-sided optical port enabling in and out coupling of light where the input waveguide begins and the output waveguide ends.

22 Claims, 11 Drawing Sheets

(51) Int. Cl.
  *G01N 33/543* (2006.01)
  *G02B 6/293* (2006.01)
  *G02B 6/30* (2006.01)
  *G02B 6/12* (2006.01)

(52) U.S. Cl.
  CPC ..... *G02B 6/29352* (2013.01); *G01N 21/7746* (2013.01); *G01N 2021/7779* (2013.01); *G02B 6/30* (2013.01); *G02B 2006/12164* (2013.01)

(56) References Cited

U.S. PATENT DOCUMENTS

2010/0119189 A1     5/2010  Nasu
2011/0305599 A1 *  12/2011  Tan ..................... G02B 6/262
                                                      422/69
2015/0109661 A1 *   4/2015  Li ...................... G02B 6/29343
                                                      359/341.4

FOREIGN PATENT DOCUMENTS

WO    WO 2008141417        11/2008
WO    WO-2013053930 A1 *    4/2013  ......... G01N 21/7746

* cited by examiner

PHOTONIC CHIPS WITH ONE SIDED OPTICAL PORTS SELF ALIGNED TO BIFURCATED FIBERS FOR THE LABEL FREE DETECTION OF BIOMOLECULAR REACTIONS THROUGH THE USE OF INTEGRATED INTERFEROMETERS AND RESONATORS

BACKGROUND

Field

The invention is directed to the field of photonic chips and methods for the label-free detection of biomolecules through monitoring the spectral and resonance shifts in on-chip integrated interferometers and resonators.

Background Information

Diagnostic devices that monitor binding reactions between a molecular probe and an analyte provide valuable information in a range of areas covering medical fields, food testing and research applications. A recognition molecule, usually a biomolecule, is immobilized on a solid support and upon interacting with the counterpart molecule in the analyte solution starts building up an adlayer that is detected by electromagnetic or mechanical methods. It is desirable the detection to be free of labels. The label free detection needs no additional reagents (labels) and assay protocol steps with obvious benefits in assay speed and costs and is valuable in reaction kinetics studies.

Photonic probing of adlayers in developing biomolecular reactions is preferable to other types of biosensing (potentiometric, impedance spectroscopy, quartz microbalance, SAW, etc.) because of the galvanic isolation of the transducer from the excitation and detection components and the optical frequency regime of operation. The galvanic isolation suppresses unwanted ionic conduction currents and drifts while the optical frequencies provide for a wide dynamic range and eliminate lower frequency interference effects (power lines or radio frequency communication devices).

In the area of optical detection, planar waveguide based interferometry or resonance is way more sensitive compared to the one-dimensional white light reflectometry [Petrou, P. S., et. al. *Real-time label-free detection of complement activation products in human serum by white light reflectance spectroscopy. Biosens. Bioelectron.* 24, 3359-3364 (2009)]. In white light reflectometry the photons probe the biomolecular layer twice compared to hundreds or thousands of times in the case of integrated waveguide based optical chips. Binding on the sensing waveguide changes the waveguide effective index which causes spectral and resonance shifts on the waveguided light. Monitoring of shifts allows for the label free detection of the analyte molecule. Spectrally resolved integrated optical devices include broadband Mach-Zehnder interferometers [Misiakos, K, et al. "*Broad-band Mach-Zehnder interferometers as high performance refractive index sensors: Theory and monolithic implementation*" Opt. Express 22, 8856-8870 (2014)] and resonators, such as ring resonators, Bragg grating waveguides and photonic crystal microcavities. Broad-band Mach-Zehnder interferometers are not susceptible to limitations characteristic of their monochromatic counterparts [Heideman, R. G. & Lambeck, P. V "*Remote opto-chemical sensing with extreme sensitivity: design, fabrication and performance of a pigtailed integrated optical phase-modulated Mach-Zehnder interferometer system*" Sens. Actuator B 61, 100-127 (1999)] and provide for much wider spectral shifts compared to resonators due to their differential nature. On the other hand, ring resonators [White I. M. & X Fan, X "*On the performance quantification of resonant refractive index sensors*" Opt. Express 16, 1020-1028 (2008)], Bragg resonators [Wang, X "*A silicon photonic biosensor using phase-shifted Bragg gratings in slot waveguide*" Journal of Biophotonics, 6, 10, 821-828, (2013)], or resonant microcavities [Passaro, Vittorio M. N.; Troia, Benedetto; La Notte, Mario; et al. "*Photonic resonant microcavities for chemical and biochemical sensing*" Rsc Advances 3,1, 25-44 (2013)] present much sharper responses at resonance wavelengths as a result of the high quality factor. Eventually both the interferometric and resonance configurations have similar limits of detection the main difference being the spectral shift detection principle: In a broad-band Mach-Zehnder interferometer white light is employed as input while the spectral shifts are detected by a spectrometer. In the resonator case the spectral shifts are not wide enough to be detected by standard spectrometers. Here the input is provided by a tunable monochromatic light source while a photodetector monitors the output optical power. The bias on the tunable source is swept causing a wavelength sweep until resonance is achieved and detected as a sudden change on the photodetector signal. The resonance wavelength is inferred from the laser bias at the time of the photodetector sudden response. With either configuration picomolar level sensitivities can be achieved [A. Psarouli, et. al. "*Monolithically integrated broad-band Mach-Zehnder interferometers for highly sensitive label-free detection of biomolecules through dual polarization optics*" Scientific Reports 5, 17600]. Therefore, if such planar waveguide based devices can be interfaced with input light sources and output detectors units through practical and straightforward methods then high sensitivity detection on an affordable, versatile and even portable platform becomes a reality. So far, such optical devices were made so that the input and output light terminals were on different, mostly opposite, sides of the photonic chip.

SUMMARY

The present invention proposes a way for coupling light in and out of an integrated interferometer or resonator through the use of photonic chips with one-sided optical ports and the employment of bifurcated fibers. The bifurcated fiber at the common end matches the input and output waveguide pair at the one-sided optical port of the planar photonic chip. This is possible by using a U turn on the main waveguide. At the same time, one branch of the bifurcated fiber is connected with its free end to a light source and the other branch with its free end to a detector unit. This way spectral and resonance shifts will be recorded in real time while the photonic chip is immersed through the end opposing the optical port into the analyte solution. The proposed method as a planar waveguide based interferometer or resonator is expected to exhibit much higher sensitivity compared to the one-dimensional white light reflectometry employed in the ForteBio Patent [Tan et al. "Fiber-optic assay apparatus based on phase-shift interferometry" U.S. Pat. No. 7,319,525 B2 Jan. 15, 2008]. Additionally, more than one interferometers resonators can be integrated as opposed to one on the ForteBio Patent.

A photonic chip based optical set-up is outlined for detecting analyte molecules through integrated optical interferometry and/or resonance. The set-up incorporates light sources, bifurcated fibers, photonic chips with one-sided optical ports and integrated interferometers/or resonators, a mechanical optical coupling module, and detector units. The photonic chip is directly interfaced with the bifurcated fiber so light enters the chip through the input fiber/input waveguide interface and light exits the chip from the same side through the output waveguide/output fiber interface. No reflection based interferometry is employed. The spectral shifts monitored at the detector unit provide a measure of the molecular adlayer built-up.

The proposed photonic chip and method for the label free detection of biomolecules is based on a photonic integrated circuit with optical inputs and outputs on the same chip side enabling light coupling in and out through a bifurcated fiber. This is achieved by a U turn on the main waveguides so that the same chip edge is receiving and simultaneously emitting. The chip features Mach-Zehnder interferometers or resonators based on planar waveguides. Spectral and resonance shifts occur when the spotted sensing windows are exposed to the analyte solutions. On theses windows the recognition molecules have been previously immobilized. In the case of Broad-Band Mach-Zehnder interferometers the input fiber supplies broad-band light to the input waveguides, this light goes through the interferometer is getting modulated and is fed back through the output waveguides to the output fiber. This fiber is directed to a spectrometer which monitors the spectral shifts induced by the binding reactions on the sensing window of the interferometer. The Mach-Zehnder configuration greatly enhances the spectral shifts and makes possible the use of commercial spectrometers as detectors. The observable in the interferometer case is the phase of the peak of the Fourier transform of the nearly sinusoidal spectrometer signal. In photonic chips with multiple interferometers each interferometer is engineered so that it has its own distinct peak in the Fourier domain and all peaks are independently tracked by monitoring their phases. In the case of resonators, the input waveguides receive light from a tunable laser source through the input fiber, the light interacts with the resonators and is fed to the output fiber through the output waveguides. The output fiber connects to a photodetector. The same main or bus waveguide can have one or more resonators. The laser bias is swept and the sudden changes in the detector signal are monitored. This way the resonance wavelength shifts are related to binding induced effective index changes. In the case of multiple resonators, the bias sweep is wide enough to include all resonators.

DETAILED DESCRIPTION

Definition of Terms

Figure 1:
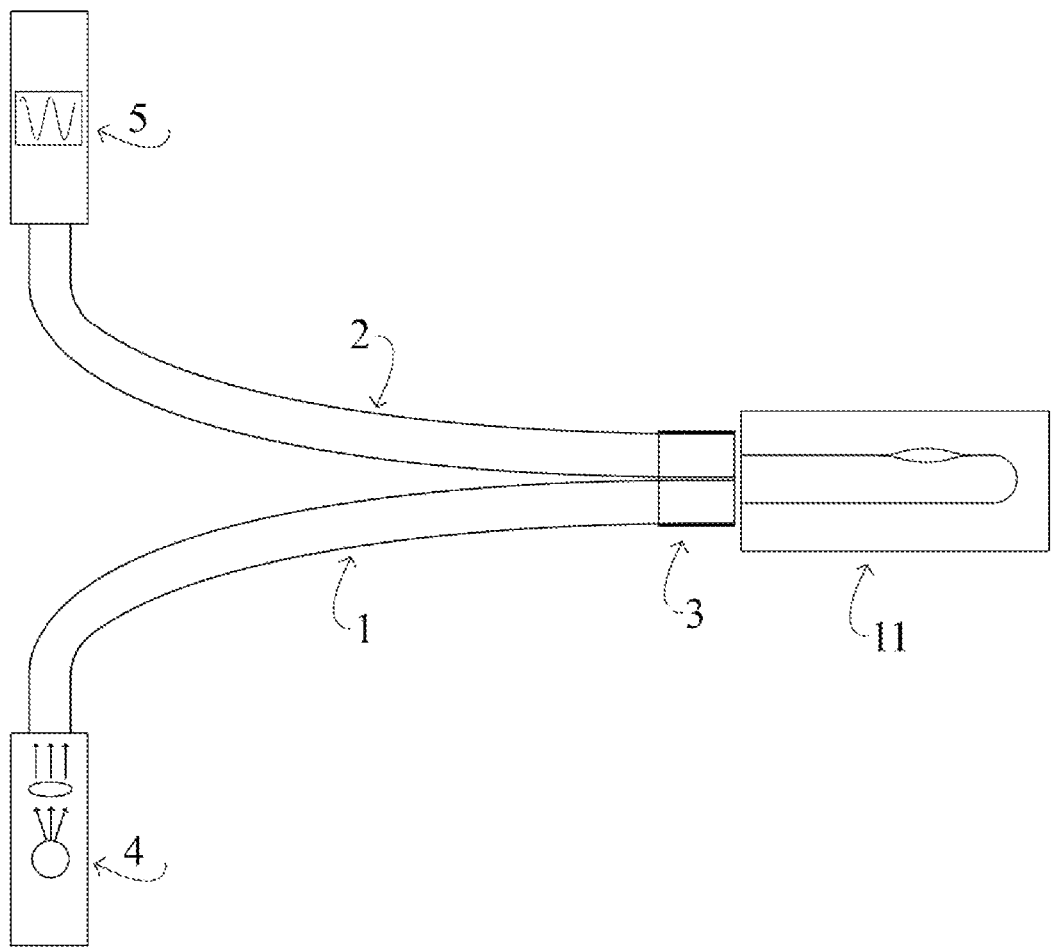
FIG. 1. A photonic chip with one-sided optical port (11) carrying a Mach-Zehnder interferometer and coupled through a bifurcated fiber to a white light source (4) and a spectrometer (5). The bifurcated fiber consists of the input fiber (1), the output fiber (2) and the common end (3)

Bifurcated fiber: A pair of optical fibers forming a Y junction. On one end the two fibers are side-by-side (common end) while the two fibers split apart towards the other free end.

Photonic Chip: A planar stack of dielectric films on appropriate substrates consisting of dielectric bottom-cladding and top-cladding layers as well as of the waveguiding core layer patterned so that planar waveguides form a photonic integrated circuit consisting of the input waveguides, the output waveguides and the Mach-Zehnder interferometers or resonators in-between. The bottom-cladding and top-cladding layers are thick enough to isolate the core layer from the substrate and any material in contact with the top-cladding. The waveguide core is made of a higher refractive index material than the bottom and top-cladding dielectric layers. The core interacts with the environment only in selected areas, sensing windows, where the top-cladding is removed. A typical choice would be silicon dioxide as top and bottom cladding layers and silicon nitride or silicon oxynitride as core. An alternative choice for the core material is silicon in case wavelengths in excess of 1200 nm are chosen. The substrate is preferentially opaque and can be insulating or semiconducting, like silicon, or metal.

Input waveguides: The part of the photonic integrated circuit that receives light from an adjacent external fiber at the photonic chip edge.

Output waveguides: The part of the photonic integrated circuit that emits light to an adjacent external fiber at the photonic chip edge.

Main waveguides: The part of the photonic integrated circuit between the input and the output waveguides. This part includes the interferometer and/or the resonator.

Photonic chips with one-sided optical port: Photonic chips where the in and out coupling of light takes place at the same photonic chip edge where the input waveguides begin and the output waveguides end.

Mach-Zehnder interferometer: A waveguide structure where the input waveguide is split into two branches by a Y junction, the two branches run in parallel before they recombine to the output waveguide through a reverse Y junction. One branch, named sensing arm, is spotted on the sensing window with the recognition or probe molecule while the other, named reference arm, is not. The sensing and reference arms have effective indices $N_s$ and $N_r$, respectively. Usually the reference arm is buried under the top-cladding layer. The light in the two branches experiences different media resulting in a phase difference at the second Y junction. For a broad-band light, the output spectrum varies proportionally to $1+\cos[2\pi(N_r-N_s)L/\lambda_0]$, where L is the sensing window length on the sensing arm and $\lambda_0$ the vacuum wavelength. The effective indices $N_r$ and $N_s$ are functions of $\lambda_0$. The two arms can be engineered by adjusting their thickness so that the cosine argument above is an almost linear function of $\lambda_0$. Under these conditions the output spectrum becomes a nearly sinusoidal function of $\lambda_0$ so that the spectral shifts are best analyzed by Fourier transform techniques. Such spectral shifts are induced as a result of the changes in $N_s$ when a molecular adlayer builds on the sensing window.

Resonator: A waveguide structure that exhibits sharp positive or negative peaks in the reflection or transmission spectra. The sharp resonance peaks occur when the vacuum wavelength of the waveguided photons is an integral submultiple of a critical length times the waveguide effective index. A change in the effective medium due to molecular binding changes the effective index and, hence, the resonance wavelength. The spectral shift is a measure of the molecular layer built-up. Such resonators include optical ring resonators, waveguides with Bragg gratings, and photonic crystal waveguides. An optical ring resonator is a planar waveguide structure where a ring waveguide in the vicinity of the main, or bus, waveguide resonates when the wavelength is an integral submultiple of the ring circumference times the effective ring index. At resonance, a sudden drop of optical power in the bus waveguide is observed. In the case of Bragg grating waveguides the critical length is twice the grating period. Similar conditions hold for photonic crystal microcavities with a more complex dependence of the resonance wavelengths on the photonic crustal geometry.

Input fiber: The one fiber of the bifurcated pair that is connected through its free end to a light source while its common end connects to the input waveguides of the photonic chip.

Output fiber: The one fiber of the bifurcated pair that is connected through its free end to a detector (spectrometer or photodetector) while its common end connects to the output waveguides of the photonic chip.

Light source: White light source in the case of the Mach-Zehnder interferometer. A tunable laser, preferably a laser diode, in the resonator case. In either case the light source apparatus supplies light into the input fiber of the bifurcated fiber. This light is broad-band in the case of the Mach-Zehnder interferometer and tunable monochromatic in the resonator case.

Spectrometer: An optoelectronic device made of an optical grating and an imaging array, usually a CCD array, that records the spectrum of the light entering the spectrometer. The light impinges on the grating under an angle and is reflected towards the imaging array that creates digital recordings of the spectrum as the reflection angle depends on the wavelength.

Detector Unit: A Spectrometer in the Mach-Zehnder case, a photodetector in the resonator case. The photodetector is either semiconductor p-n junction ionization based device, or a heat sensing element, like a thermopile.

Mechanical optical coupling module: A two-port mechanical part placed between the bifurcated fiber common end and the photonic chip one-sided optical port to provide for the optical alignment of the bifurcated input and output fiber with the input and output waveguide of the photonic chip. One port matches the outer dimensions of the bifurcated fiber common end and the other port in the form of a rectangular slit matches the photonic chip cross section. It is light tight and provides for the optical coupling between the input-output bifurcated fibers to the integrated input-output waveguides, respectively.

Sensing window: Part of the sensing arm in the Mach-Zehnder case, ring waveguide in the ring resonator case, the Bragg grating in the Bragg grating resonator case, and the microcavity in the photonic crystal case. The sensing window is functionalized by immobilizing the probe molecules on it.

Probe molecules: The molecules that are coated on the sensing windows. They can be proteins, hormones, DNA fragments, or other types of molecules that specifically react with a counterpart molecule of interest in the sample to be analyzed.

Spotted chip: A Photonic chip with one or more sensing windows where one or more recognition molecules have been immobilized.

Analyte molecule: A molecule of analytical interest that will react specifically with probe molecule immobilized on the sensing window.

Concept Outline

Figure 2:
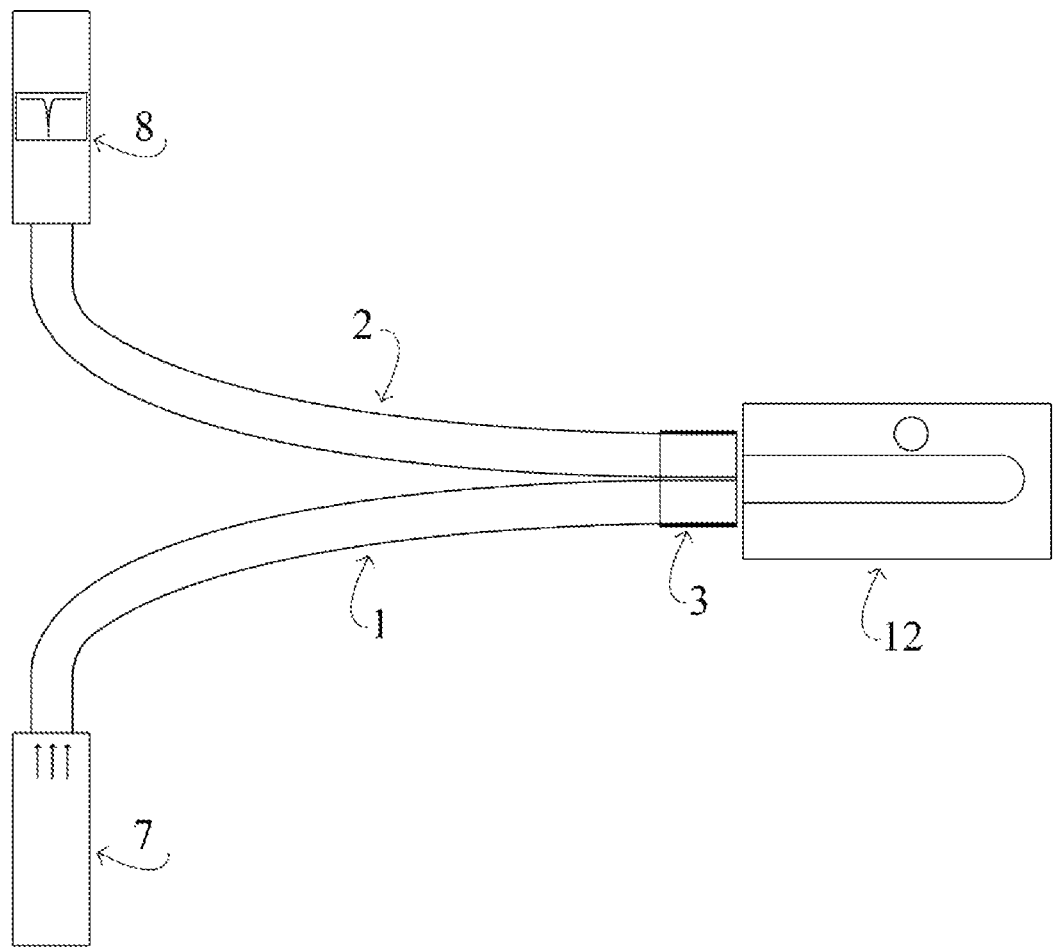
FIG. 2. A photonic chip with one-sided optical port (12) carrying a ring resonator and coupled through a bifurcated fiber to a tunable monochromatic light source (7) and a photodetector (8). The bifurcated fiber consists of the input fiber (1), the output fiber (2), and the common end (3).

The schematics in FIG. 1 and FIG. 2 show the two basic configurations of photonic chips with one-sided optical ports and optically coupled to a bifurcated fiber: A Mach-Zehnder interferometer (FIG. 1), and a ring resonator (FIG. 2). In FIG. 2 the ring resonator exemplifies the resonator case. The two figures illustrate the light source coupling light to the input fiber (1) of the bifurcated pair, the output fiber (2) being driven to the detector unit while the photonic chips (11,12) with their input and output waveguides are optically butt coupled to the bifurcated fiber common end. The photonic chip in FIG. 1 integrates the Mach-Zehnder interferometer (11) and in FIG. 2 the ring resonator (12) along the input and output waveguides. Through the output fiber (2), the interferometer (11) is coupled to a spectrometer (5) in FIG. 1, while the resonator is coupled to a photodetector (8) in FIG. 2. The light source will be a white one (4) in the case of a Mach-Zehnder interferometer in FIG. 1 or a tunable monochromatic laser source (7) in the case of a ring resonator in FIG. 2. In the interferometer case of FIG. 1, white light (4) coupled to the input fiber (1) and then to the on-chip input waveguide is getting modulated through the Mach-Zehnder interferometer and then is fed to the spectrometer (5) through the output waveguide and output fiber (2). Spectral shifts of the modulated light reveal the built up of a molecular adlayer on the sensing window of the spotted chip. In the resonator case of FIG. 2, tunable monochromatic light (7) coupled to the input fiber (1) and then to the on-chip input waveguide interacts with the ring resonator and then is fed to the photodetector (8) through the output waveguide and output fiber (2). The bias on the tunable source is swept until a sudden drop is detected at the photodetector. The bias point at the sudden drop is indicative of the built-up of a molecular adlayer on the sensing window of the spotted chip.

Figure 3:
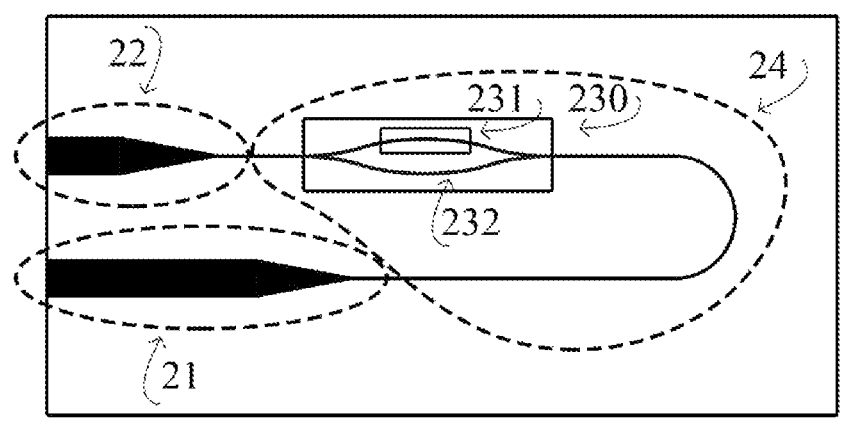
FIG. 3. A photonic chip with one-sided optical port carrying a Mach-Zehnder interferometer (230). The main waveguide (24) with the U turn is shown connected with tapers to the input (21) and output (22) waveguides. Also shown are the sensing arm (231), with the sensing window, and the reference (232) arm.
Figure 4:
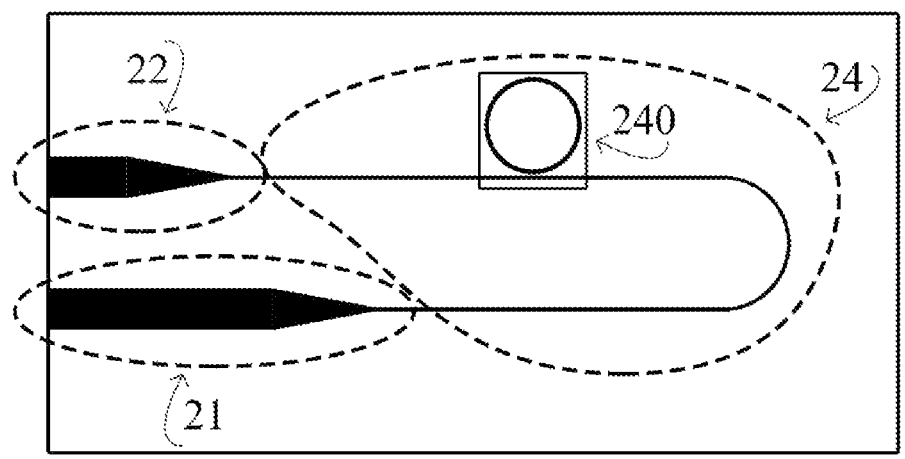
FIG. 4. A photonic chip with one-sided optical port carrying a ring resonator (240). The main waveguide (24) with the U turn is shown connected with tapers to the input (21) and output (22) waveguides FIG. 5. A photonic chip with one-sided optical port (31) carrying two Mach-Zehnder interferometers with parallel input and output waveguides and coupled through a bifurcated fiber to a white light source (4) and a spectrometer (5). The bifurcated fiber consists of the input fiber (1), the output fiber (2), and the common end (3).

The schematics in FIG. 3 and FIG. 4 illustrate the inner structure of the photonic chips and the waveguides. The input waveguide (21) is aligned to the input fiber, the output waveguide (22) to the output fiber while the main waveguide (24) contains the interferometer (230) or the resonator (240). The sensing window (231) of the interferometer in FIG. 3 is spotted with the probe molecules as opposed to the reference arm 232 that is not spotted by burying it under a thick top-cladding layer. Similarly, in the resonator case of FIG. 4 the ring waveguide (240) is spotted. The input (21) and output (22) waveguides have appropriate thickness and width to increase the coupling efficiency to the input and output bifurcated fibers and to minimize propagation losses due to line edge roughness. The interferometers or the resonators are connected with tapers in the horizontal plane or in the vertical direction to the input and output waveguides. At the U turn the waveguide has appropriate curvature to minimize bending losses.

Figure 5:
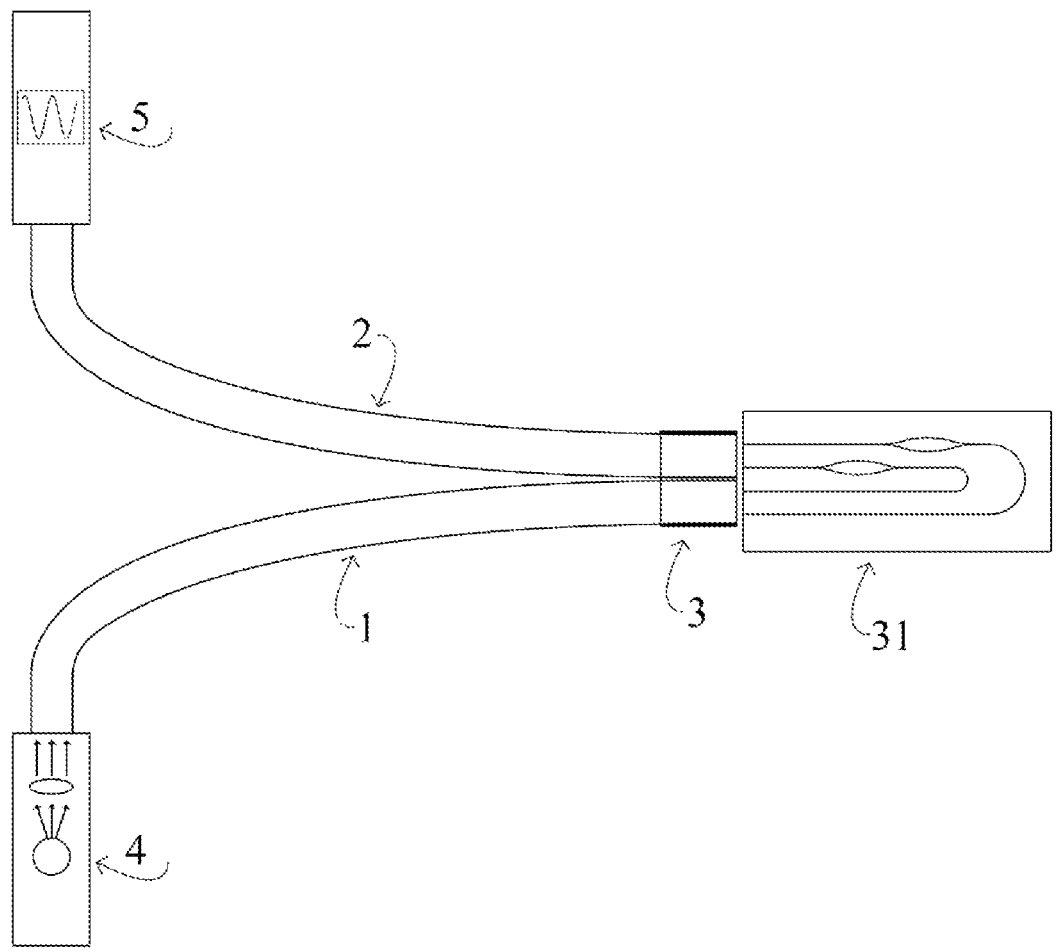

In FIG. 5 a photonic chip (31) with two Mach-Zehnder interferometers is shown. The input fiber is much wider than the total width of the input waveguide pair and both waveguides are equally excited. The output fiber collects the light of both output waveguides. Demultiplexing is achieved by tuning the output spectrum oscillation frequencies of either interferometer at well separated values. The two interferometers are engineered by thinning the reference and/or sensing arm in a way to produce sinusoidal modulations on their output spectrum at different frequencies [Misiakos, K., et al. *"Broad-band Mach-Zehnder interferometers as high performance refractive index sensors: Theory and monolithic implementation" Opt. Express* 22, 8856-8870 (2014)]. If Fourier transform is applied on the composite spectrum collected by the output fiber and sensed by the spectrometer, then two distinct narrow bands are obtained at different wavenumber frequencies, as will be shown in FIG. 11. The individual spectral shifts due to biomolecular binding are obtained by tracking the phase of the complex Fourier Transform value at the peaks. Such a multiplexing capability provides the opportunity to integrate in addition to the reaction interferometer a blank interferometer for base line corrections. The ability to track two interferometers at a time is a distinct advantage over the reflection probe based devices. Obviously, more than two interferometers can be multiplexed by selecting for each one output spectrum oscillation frequencies far apart from the nearest neighbor.

Figure 6:
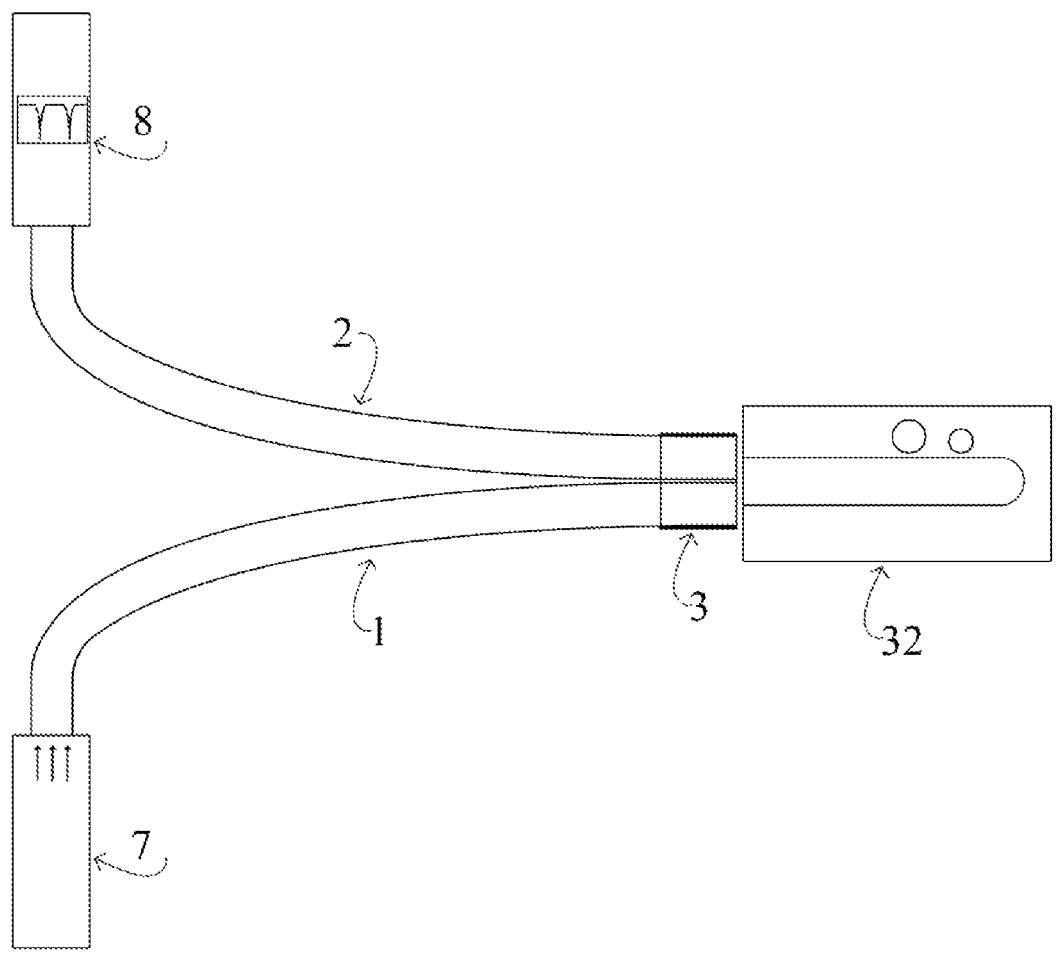
FIG. 6. A photonic chip with one-sided optical port (32) carrying two ring resonators on the same bus (main) waveguide and coupled through a bifurcated fiber to a tunable monochromatic light source (7) and a photodetector (8). The bifurcated fiber consists of the input fiber (1), the output fiber (2) and the common end (3).

If the resonator solution is chosen, as in FIG. 6, then two or more resonators can be incorporated in the photonic chip (32). The example in FIG. 6 demonstrates the ability to have two different diameter rings coupled to the same main or bus waveguide resulting in two different sequences of resonance wavelengths. The deconvolution of the signals at the outputs is achieved by the different resonance wavelengths and the ability of the tunable monochromatic light source to scan these wavelengths with a bias sweep.

Figure 7:
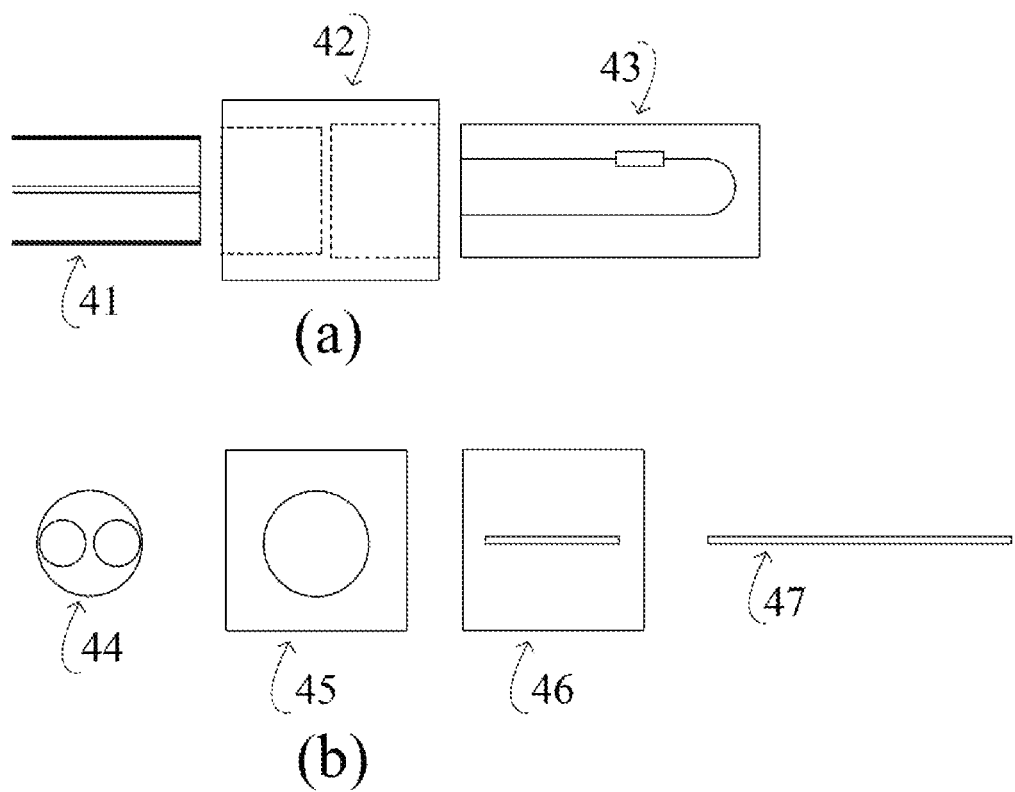
FIG. 7. The mechanical optical coupling module for the fiber-chip alignment, top view (a) and side views (b). The module top view (42) in (a) is shown in alignment with the bifurcated fiber common end (41) and the photonic chip (43) carrying the interferometer or resonator. In side view (a), the cross section of the bifurcated fiber common end (44) has the same outer diameter as the corresponding aperture on the module side view (45). The other module side view facing the photonic chip (46) has a rectangular aperture that exactly fits the one-sided optical port of the photonic chip shown in side view (47).

The mechanical optical coupling module for the bifurcated fiber-photonic chip alignment is shown in FIG. 7 (a,b). The purpose of the module (42) is to align the input and output waveguides of the photonic chip (43) to the input and output fibers at the bifurcated fiber common end (41), as shown in top view in FIG. 7a. The photonic chip will carry either Mach-Zehnder interferometers or resonators. From side view, FIG. 7b, the module has two sides with openings, one (45) adjacent to the bifurcated fiber common end (44) and another (46) adjacent to the photonic chip (47). The module side (45) facing the bifurcated fiber has an aperture with the same diameter as the fiber common end (44). The other module side (46) facing the photonic chip has a rectangular slit that exactly fits the one-sided optical port of the photonic chip (47). From top view, the bifurcated fiber common end (41) and the photonic chip (43) are inserted from the two opposing sides of the module 42 and travel inside until the stop points. The optical alignment of the bifurcated input and output fiber with the input and output waveguide of the photonic chip is achieved through guides or marks on the bifurcated fiber and the mechanical module. The upper side of the rectangular slit contacts the top-cladding layer of the photonic chip while the lower side contacts the photonic chip substrate bottom plane.

Figure 8:
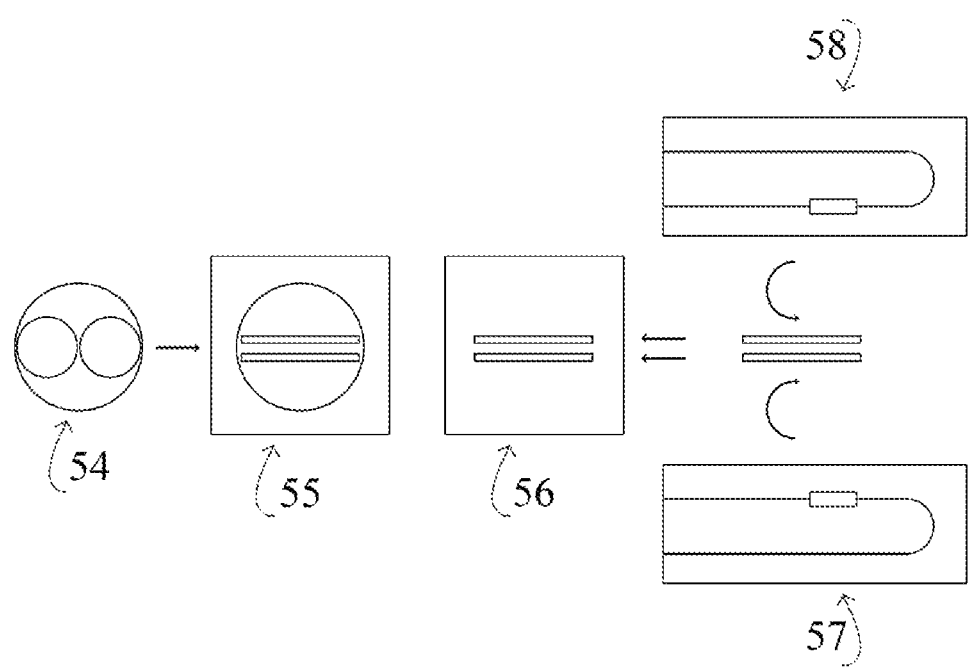
FIG. 8. A mechanical optical coupling module for interfacing two photonic chips. One module side (55) fits the bifurcated fiber common end (54), shown in cross section, while the other module side (56) fits the two photonic chips. Two symmetric photonic chips (57), (58) are placed face-to-face fitting the respective rectangular and symmetrically placed slits on the module side (56) facing the photonic chip. The distance between the chips is much shorter than the diameter of the bifurcated input and output fibers. The input and output waveguides on the two photonic chips are symmetrically placed so that they match each other when placed face-to-face and are both effectively coupled with the input and output bifurcated fibers, respectively.

Another configuration of mechanical optical coupling module is shown in FIG. 8. Two symmetric photonic chips (58), (57) are placed face-to-face against the bifurcated fiber common end and at a distance much shorter than the fiber diameter by fitting into the respective rectangular and symmetrically placed slits of the module side (56) facing the photonic chip. The input and output waveguides on the two photonic chips are placed symmetrically so that they match each other when face-to-face. On the other module side (55) facing the bifurcated fiber, the aperture exactly fits the outer diameter of the bifurcated fiber common end (54). The two photonic chips are excited by the same input fiber and supply their output light to the output fiber though their output waveguides. Multiplexing is enabled by using distinctly different oscillation frequencies, when the interferometers are involved, or different resonance wavelengths in the resonator case. The two chips can be spotted independently, and they can act as two independent probes on the same sample solution. They can also take in liquid samples through capillary action provided the two surfaces are hydrophilic.

Example

Figure 9:
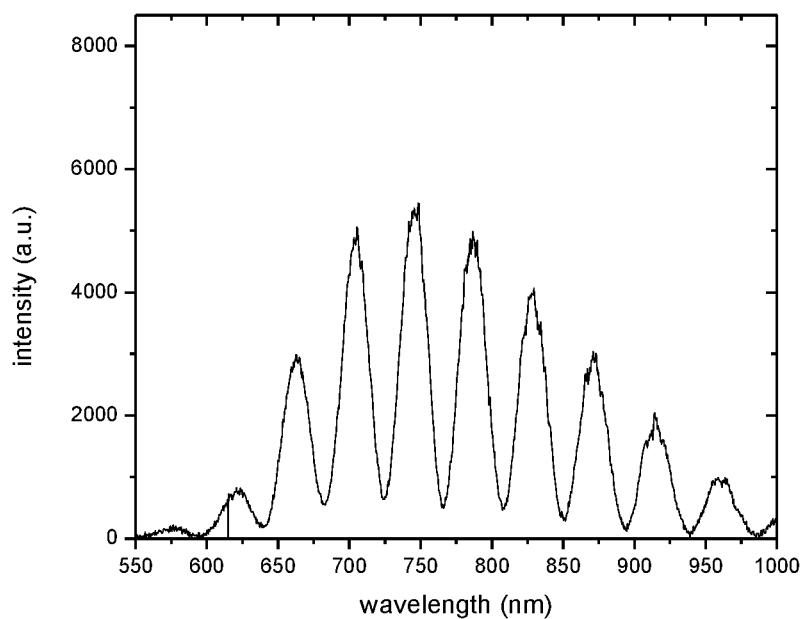
FIG. 9. Output spectrum of a broad-band Mach-Zehnder interferometer. The sensing arm has a thickness of 150 nm and the reference arm a thickness of 167 nm. The sensing window is 600 microns. Here the core is made of silicon nitride while the top and bottom-cladding layers are silicon dioxide.
Figure 10:
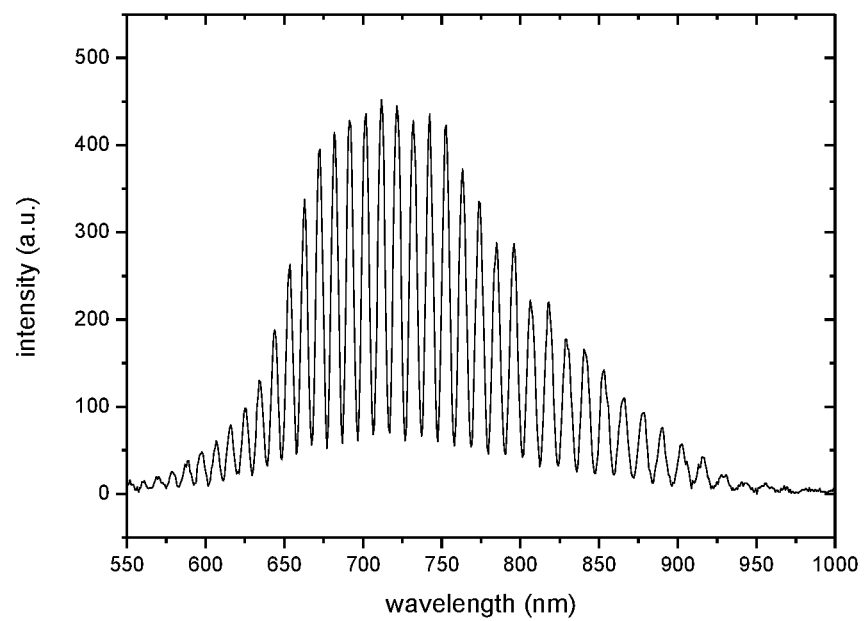
FIG. 10. Output spectra of a broad-band Mach-Zehnder interferometer. The sensing arm has a thickness of 125 nm and the reference arm a thickness of 155 nm. The sensing window is 600 microns. Here the core is made of silicon nitride while the top and bottom-cladding layers are silicon dioxide.

An example of how different oscillatory behavior is obtained at the output of Mach-Zehnder interferometers is shown in FIG. 9, and FIG. 10 where the output spectra of two different Mach-Zehnder interferometers are shown. The two interferometers are engineered through thinning of the sensing arm core so that when excited by broad-band light different frequencies appear in the output spectra depending on the thinning extent. In FIG. 9 the sensing arm has a thickness of 150 nm and the reference arm a thickness of 167 nm while in FIG. 10 the sensing arm has a thickness of 125 nm and the reference arm a thickness of 155 nm. A thinning of the nitride core by 17 nm creates the oscillations in FIG. 9, while a thinning by 30 nm the much higher oscillations of FIG. 10.

Figure 11:
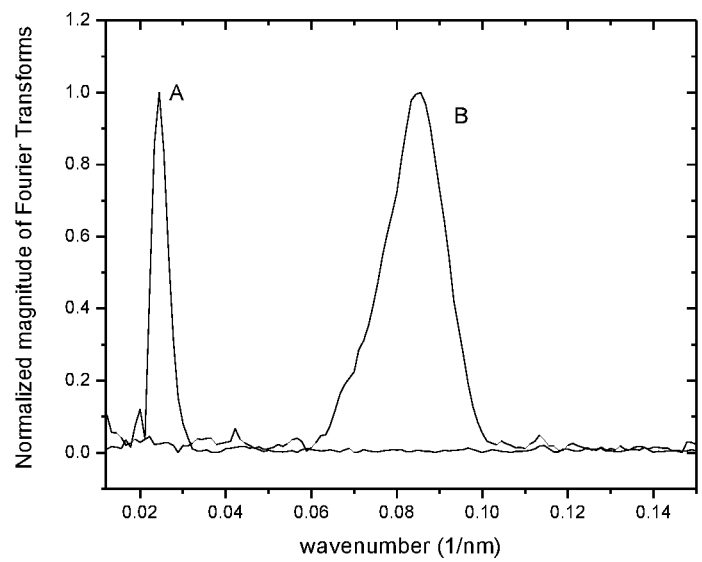
FIG. 11. Fourier transform in the wavenumber domain of the oscillatory output data of the interferometers in FIG. 9 and FIG. 10. Two distinct peaks appear corresponding to the two oscillation frequencies. The two peaks have been normalized to unity.

The composite spectrum or the sum of the two spectra at the detector site can be deconvoluted by Fourier transform in the wavenumber domain. In such a case, as shown in FIG. 11, two distinct narrow bands, A and B, are obtained corresponding to the interferometers in FIG. 9 and FIG. 10, respectively. Each interferometer is characterized by each own peak. So, the individual spectral shifts can be deconvoluted by tracking the phase of the complex Fourier Transform value at the peaks. Similar results can be obtained by keeping the sensing arms at a fixed thickness while choosing higher thickness for the reference arms. Again the higher the core thickness difference between the reference and the sensing arm the higher the oscillation frequency. Another approach would be to choose different sensing window lengths for the two interferometers while keeping the same core thickness for the two arms. Such a multiplexing capability provide the opportunity to integrate in addition to the reaction interferometers a blank interferometer for base line corrections.

ADVANTAGES

Photonic chips with one-sided optical ports can exchange in either direction light signals with bifurcated fibers through the use of a simple mechanical optical coupling module. This way there is no need for bulk optics, like lenses and optical mounts, and the photonic chip can be employed as a bio-chemical probe following spotting of the sensing windows by the appropriate probe molecules. In its simplest configuration the spotted chip can be immersed through the side opposing the optical port in a microwell to monitor a binding reaction. The probe molecules immobilized on the sensing window will react with the counterpart analyte molecules and will produced spectral and resonance shifts on the waveguided light. The waveguided light is brought in from the light source via the input fiber and the input fiber-input waveguide interface. The output spectral shifts or intensity variations will be driven into the detector unit via the output fiber and the output fiber-output waveguide interface. The single optical port communication with the external light source and detector allows the free chip side and most of the chip to be used as an immersible optical probe. The method employs planar waveguides in the form of interferometers or resonators and no reflection interferometry is used. Compared to white light reflectometry based techniques is far more sensitive and can integrate more than one interferometer or resonator. This way multianalyte measurements, including blanc waveguides, are possible.

The invention claimed is:

1. A photonic chip configured to be optically butt-coupled with a bifurcated fiber, the photonic chip comprising: a plurality of non-intersecting input waveguides and non-intersecting output waveguides configured to be optically butt-coupled with a common end of a bifurcated fiber; one of at least one Mach-Zehnder interferometer and at least one resonator; and a one-sided optical port enabling in and out butt coupling of light where the input waveguides begin and the output waveguides end.

2. The photonic chip of claim 1, wherein the one of the at least one Mach-Zehnder interferometer and the at least one resonator comprises at least one Mach-Zehnder interferometer.

3. The photonic chip of claim 2, wherein the at least one Mach-Zehnder interferometer comprises more than one Mach-Zehnder interferometer each having a different output spectrum oscillation frequency.

4. The photonic chip of claim 1, wherein the one of the at least one Mach-Zehnder interferometer and the at least one resonator comprises at least one resonator.

5. The photonic chip of claim 4, wherein the at least one resonator comprises more than one resonator each having a different resonance wavelength.

6. The photonic chip of claim 1, wherein the input and output waveguides are configured to be optically aligned with respective adjacent input and output fibers of the bifurcated fiber by a mechanical optical coupling module having one side that is disposed adjacent to the one-sided optical port of the photonic chip and another side that is disposed adjacent to the bifurcated fiber common end to permit the input waveguides to receive light from the input fibers and permit the output waveguides to emit light to the output fibers; and wherein the one-sided optical port is configured for removable connection to the mechanical optical coupling module by an opening at the one side of the mechanical optical coupling module receiving the one-sided optical port so that a top-cladding layer of the photonic chip contacts an upper side of the opening and a a substrate bottom plane of the photonic chip contacts a lower side of the opening to provide for the proper rotation of the bifurcated fiber common end so that a line connecting centers of the input and output fibers matches an edge of the one-sided optical port and the input and output waveguides are adjacent and optically butt coupled to the input and output fibers.

7. The photonic chip according to claim 1, further comprising at least one main waveguide containing the one of the at least one Mach-Zehnder interferometer and the at least one resonator, the at least one main waveguide being configured with a turn substantially in the shape of a "U" for connection to the input and output waveguides to enable in and out coupling of light at the one-sided optical port.

8. The photonic chip according to claim 1, wherein the one of the at least one Mach-Zehnder interferometer and the at least one resonator comprises one of a plurality of Mach-Zehnder interferometers and a plurality of resonators; and further comprising a plurality of main waveguides each containing a respective one of the plurality of Mach-Zehnder interferometers or the plurality of resonators and connected to respective ones of the plurality of input and output waveguides.

9. An apparatus for the detection of analytes, comprising:
at least one photonic chip having a plurality of non-intersecting input waveguides and non-intersecting output waveguides, at least one Mach-Zehnder interferometer, and a one-sided optical port enabling in and out coupling of light where the input waveguides begin and the output waveguides end;
a bifurcated fiber formed of an input fiber and an output fiber, the bifurcated fiber facing at a common end thereof the one-sided optical port of the at least one photonic chip while a free end of the input fiber is connected to a white light source and a free end of the output fiber is connected to a spectrometer;

a mechanical optical coupling module placed between the bifurcated fiber common end and the one-sided optical port of the at least one photonic chip to provide non-reflective coupling between the bifurcated fiber and the at least one photonic chip and provide for the proper rotation of the bifurcated fiber common end so that a line connecting centers of the input and output fibers of the bifurcated fiber matches an edge of the one-sided optical port and the input and output waveguides are adjacent and optically butt coupled to the input and output fibers; and a probe molecule immobilized on a sensing window of the at least one Mach-Zehnder interferometer of the at least one photonic chip to create spectral shifts on an output spectrum upon binding with analyte molecules by immersing the sensing window into an analyte solution or by adding an analyte solution drop on the sensing window.

10. The apparatus of claim 9, wherein the sensing window is hydrophilic.

11. The apparatus of claim 9, wherein a different probe molecule is immobilized on the sensing window of the at least one photonic chip.

12. The apparatus of claim 9, wherein the at least one Mach-Zehnder interferometer of the at least one photonic chip comprises more than one Mach-Zehnder interferometer each having a different output spectrum oscillation frequency; and further comprising a plurality of main waveguides each containing a respective one of the Mach-Zehnder interferometers and being configured with a turn substantially in the shape of a "U" for connection to respective ones of the plurality of input and output waveguides to enable in and out coupling of light at the one-sided optical port.

13. The apparatus of claim 9, wherein the at least one photonic chip comprises two symmetric photonic chips with different spectrum oscillation frequencies which when placed face-to-face the input and output waveguides match each other; wherein the bifurcated fiber faces at the common end the one-sided optical port of the two photonic chips; and wherein the mechanical optical coupling module is placed between the bifurcated fiber common end and the two photonic chips so that the two photonic chips face each other and the input and output waveguides are aligned with the bifurcated input and output fibers, respectively; and wherein the probe molecules are independently immobilized on sensing windows of the two photonic chips to create spectral shifts on the output spectrum upon binding with the analyte molecules either by immersing the sensing windows into an analyte solution or by employing capillary forces to transfer a sample between the two photonic chips.

14. The apparatus of claim 9, wherein the mechanical optical coupling module comprises a mechanical part having two ports, one of the two ports matching outer dimensions of the bifurcated fiber common end, and the other of the two ports being in the form of a rectangular slit matching a cross-section of the at least one photonic chip so that a top-cladding layer of the photonic chip contacts an upper side of the slit and a substrate bottom plane of the photonic chip contacts a lower side of the slit.

15. An apparatus for the detection of analytes, comprising:

at least one photonic chip having a plurality of non-intersecting input waveguides and non-intersecting output waveguides, at least one resonator, and a one-sided optical port enabling in and out coupling of light where the input waveguides begin and the output waveguides end;

a bifurcated fiber formed of an input fiber and an output fiber, the bifurcated fiber facing at a common end thereof the one-sided optical port of the at least one photonic chip while a free end of the input fiber is connected to a tunable monochromatic light source and a free end of the output fiber is connected to a photodetector;

a mechanical optical coupling module placed between the bifurcated fiber common end and the one-sided optical port of at least one photonic chip to provide non-reflective coupling between the bifurcated fiber and the at least one photonic chip and provide for the proper rotation of the bifurcated fiber common end so that a line connecting centers of the input and output fibers of the bifurcated fiber matches an edge of the one-sided optical port and the input and output waveguides are adjacent and optically butt coupled to the input and output fibers; and a probe molecule immobilized on a sensing window of the at least one resonator to create resonance wavelength shifts upon binding with analyte molecules by immersing the sensing window into an analyte solution or by adding an analyte solution drop on the sensing window.

16. The apparatus of claim 15, wherein the sensing window is hydrophilic.

17. The apparatus of claim 15, wherein a different probe molecule is immobilized on the sensing window of the at least one photonic chip.

18. The apparatus of claim 15, wherein the at least one resonator of the photonic chip comprises more than one resonator each having a different resonance wavelength; and further comprising a plurality of main waveguides each containing a respective one of the resonators and being configured with a turn substantially in the shape of a "U" for connection to respective ones of the plurality of input and output waveguides to enable in and out coupling of light at the one-sided optical port.

19. The apparatus of claim 15, wherein the at least one photonic chip comprises two symmetric photonic chips with different resonance wavelengths which when placed face-to-face the input and output waveguides match each other; wherein the bifurcated fiber faces at a common end thereof the one-sided optical port of the two photonic chips; wherein the mechanical optical coupling module is placed between the bifurcated fiber common end and the two photonic chips so that the two photonic chips face each other and the input and output waveguides are aligned with the bifurcated input and output fibers, respectively; and wherein the probe molecules are independently immobilized on sensing windows of the two photonic chips to create resonant wavelength shifts upon binding with analyte molecules either by immersing the sensing windows into the analyte solution or by employing capillary forces to transfer a sample between the two photonic chips.

20. The apparatus of claim 15, wherein the mechanical optical coupling module comprises a mechanical part having two port, one of the two ports matching outer dimensions of the bifurcated fiber common end, and the other of the two ports being in the form of a rectangular slit matching a cross-section of the at least one photonic chip so that a top-cladding layer of the photonic chip contacts an upper side of the slit and a substrate bottom plane of the photonic chip contacts a lower side of the slit.

21. The apparatus of claim 9, wherein the mechanical optical coupling module has one side disposed adjacent to the one-sided optical port of the at least one photonic chip and another side disposed adjacent to the bifurcated fiber common end, the one-sided optical port being removably connected to the mechanical optical coupling module by an opening at the one side of the mechanical optical coupling module receiving the one-sided optical port so that a top-cladding layer of the at least one photonic chip contacts an upper side of the opening and a substrate bottom plane of the at least one photonic chip contacts a lower side of the opening.

22. The apparatus of claim 15, wherein the mechanical optical coupling module has one side disposed adjacent to the one-sided optical port of the at least one photonic chip and another side disposed adjacent to the bifurcated fiber common end, the one-sided optical port being removably connected to the mechanical optical coupling module by an opening at the one side of the mechanical optical coupling module receiving the one-sided optical port so that a top-cladding layer of the at least one photonic chip contacts an upper side of the opening and a substrate bottom plane of the at least one photonic chip contacts a lower side of the opening.

* * * * *